United States Patent [19]

Strickman et al.

[11] 4,323,656

[45] Apr. 6, 1982

[54] POLYURETHANE SPONGES MANUFACTURED WITH ADDITIVE DISPERSED THEREIN

[76] Inventors: Robert L. Strickman, 729 Handwerg Dr., River Vale, N.J. 07675; Melvyn B. Strickman, Academy St., Shiloh, N.J. 08353

[21] Appl. No.: 955,881

[22] Filed: Oct. 30, 1978

Related U.S. Application Data

[63] Continuation of Ser. No. 305,870, Nov. 13, 1972, abandoned.

[51] Int. Cl.$^3$ .................. A47L 13/17; C08G 18/16; C08J 5/14; C11D 17/04
[52] U.S. Cl. .................. 521/109; 15/104.93; 15/244 C; 252/91; 252/92; 252/134; 252/174; 252/DIG. 16; 521/122; 521/125
[58] Field of Search .................. 252/92, 93, 117, 129, 252/130, 134, 174, DIG. 2, DIG. 5; 15/244 B, 244 C, 104.93; 521/109, 122, 125, 905

[56] References Cited

U.S. PATENT DOCUMENTS

| | | | |
|---|---|---|---|
| 3,252,775 | 5/1966 | Tocci-Guilbert | 521/109 X |
| 3,293,684 | 12/1966 | Tundermann | 15/244 X |
| 3,570,036 | 3/1971 | Gilchrist | 15/244 X |
| 3,810,841 | 5/1974 | Richter | 252/91 |

OTHER PUBLICATIONS

Vierling et al.; "Formulating Chemical Specialties with Silicones", *Soap & Chemical Specialties*, May 1967, pp. 96, 98 and 100.

*Primary Examiner*—Dennis L. Albrecht
*Attorney, Agent, or Firm*—Duffield & Lehrer

[57] ABSTRACT

This disclosure teaches synthetic polyurethane sponges manufactured with at least 5% of one or more additives dispersed therein. The additives may be soap, lotions, detergents, pesticides, lanolin, scouring particles, silicone oils, bath oils, or the like or combinations thereof. The sponges' skeletons are developed by reaction of a polyether or a polyester with a suitable isocyanate in the presence of a catalyst with the additives entrapped in voids of the sponges. An additive bearing material, i.e. a carrier material containing the additive is prepared. The carrier material is then mixed into a foam forming reaction mass. By this expedient the additive does not impair desired foam formation. The sponges are provided with high liquid absorbency and fine "hand" by virtue of manufacturing methods and specific catalysts employed.

1 Claim, No Drawings

POLYURETHANE SPONGES MANUFACTURED WITH ADDITIVE DISPERSED THEREIN

This is a continuation of application Ser. No. 305,870, filed Nov. 13, 1972, now abandoned.

INVENTION

This teaching is directed to inclusion of relatively large portions of soaps, lotions, detergents, pesticides, lanolin, scouring particles, silicone oils, bath oils or the like or combinations thereof in resilient polyurethane sponges and to methods of manufacturing same. Such sponges may be used for human bathing, animal bathing, washing dishes, scouring pots and pans, washing automobiles and various similar functions. In general terms the polyurethane synthetic sponge skeletons here contemplated come within known urethane foam manufacture. The foam structures are developed by interaction of polyethers or polyesters with isocyanates. Dispersion of the additives throughout the voids of the sponges and fine "hand" are achieved by specific manufacturing methods and by means of catalysts employed.

Because of advantageous characteristics of soaps, lotions, detergents, pesticides, lanolin, scouring particles, silicone oils, bath oils or the like or combinations thereof, it occurred to us that there would be substantial advantages in dispersing higher contents of these additives than has been achieved heretofore in sponges of the character described. An indication of the problems involved can be gleaned by considering silicone oils which are typical for such additives (except for scouring particles). It is known that silicone oils are foam depressants, as are the other additives herein mentioned. Silicone oils and other surface active agents reduce surface tension of foaming systems, resulting in foams having small and uniform cells. Because of their surface activity, silicone oils delay foam collapse by decreasing initial bubble size and by delaying breaking of large bubbles. In polyurethane foams the cell size decreases with increasing concentration of silicone oils until it reaches a concentration, usually of about 1 part per 100 parts of prepolymer, when foam collapse occurs. Foam collapse occurs at additive concentrations of approximately the same order for the other additives herein mentioned (except for scouring particles). By way of example in foam stabilizing the preferred range of dimethylsilicone oils is usually between 0.3 and 0.7 parts per 100 parts prepolymer. Very low viscosity (10, 50, and 100 centistokes) dimethylsilicone oils are widely employed, with the 50 centistoke oil being used most frequently. As viscosity of the silicone oils decreases, the silicone oils' requirement decreases, but the usable range of silicone oils' concentration becomes narrower. Such use of silicone oils is for the purpose of obtaining uniform cell structure. Concentrations of silicone oils and/or other reactive additives in the order of 10 to 25 times those used heretofore for foam stabilizing are here taught to be dispersed throughout synthetic polyurethane sponges. These and higher concentrations of additives are achievable by this invention, even though such additives are generally regarded to be active ingredients in the foam forming mechanism.

Sponges with silicone oils dispersed therein are especially suitable for cleaning and/or polishing automobile bodies and the like. Soaps, lotions, detergents, lanolin and bath oils are useful additives in sponges used for bathing. Pesticides are suitable in such sponges employed in bathing of pets. The sponges manufactured according to this method constitute inexpensive carriers for transporting these additives as well as excellent applicators thereof.

In pondering the problem as to how to disperse substantial quantities of additives throughout the sponges, it occurred to us that it would be possible to introduce the additives into a foam forming mass in such a way that the composition undergoing foam formation was insulated from foam depressing effects of the additives. We discovered that when silicone (for example) is incorporated in a suitable vehicle or carrier material, the combination of the vehicular material with the silicone can be included in the reaction mass undergoing foam formation, without impairment of the foam formation. Accordingly we manufacture sponges containing high contents of additives by preliminarily preparing an additive bearing material, i.e. a carrier material containing the additive, which carrier material is then mixed into the foam forming reaction mass; and does not impair desired foam formation.

We achieve by this invention a supporting sponge skeleton having a cell structure ranging from unicellular (closed) to multicellular (open) characteristics, as well as combinations of both of said cellular characteristics. When the sponges comprise a unicellular structure, the additive is entrapped in individual cells and becomes available during the course of the use of the sponges because of rupturing of cells in mechanical handling of the sponges. Such physical disposition of additives allows for slow release thereof; and accordingly, provides for availability of the entrapped additives throughout the life of the sponges.

Another object of this invention is to provide (where desired) in synthetic polyurethane sponges high contents of abrasives having suitable grit sizes. This object is achieved by virtue of our discovery that it is possible to incorporate a large quantity of abrasive grits (and/or comminuted cleaning materials) in a fluid mixture of synthetic foam ingredients as well as effecting rapid rise, gelation and cure thereof to assure uniformity of dispersion of the abrasive in the finished sponges. We discovered that the unique results of this aspect of the invention are achieved when the abrasive grits, at the time of incorporation thereof in the synthetic foam forming ingredients are sufficiently hot so that the heat of the grits is transferred to the foam forming ingredients, thereby accelerating gelation and curing so that formation of the foam skeleton is completed within 3 to 5 minutes. The sponges can have a grit-to-resin content in the order of 5-6 parts of the grits to 1 part of the resin.

We have also found that, in manufacturing synthetic polyurethane sponges having high grit contents, besides using the well known catalysts customarily employed in catalyzing the ineraction of the polyethers or the polyesters with the diisocyanates, we can use alginates, for example, alkali metal or ammonium salts of alginic acid. These alginates are surprisingly not only excellent catalysts, but also aid in keeping the grits uniformly dispersed in the fluid reacting mass during the rising and gelation of the resin mixture undergoing polymerization.

Products according to this aspect of the invention can have a grit-to-resin content of the order of 5-6 parts of the grits to 1 part of the resin. Among the products made in accordance with this aspect of the invention are:

Household scouring pads in which the grit-to-resin contents are of the order of 5–6:1.

A household soap product having a detergent and/or a soap-to-resin content of the order of about 4:1.

A car wash product having a synthetic detergent-to-resin content of the order of about 4:1.

A floor cleaning product, based on a combination of soap, synthetic detergent and abrasive, whereof the solids (cleansing agents) content is of the order of 4–5:1, the soap-to-synthetic detergent-to-abrasive ratio of said solids being of the order of 1.25:1.25:3.5.

An upholstery cleaner having a high foaming synthetic detergent-to-resin content of about 4:1.

A metal cleaning product containing synthetic detergent, soap and abrasive, whereof the total solids-to-resin content is 5:1, the abrasive portion of said solids being from 2 to 3 times that of the synthetic detergent plus the soap, these latter two being used in approximately equal proportions.

Industrial cleaning products, as for use in cleaning aluminum sheets, whereof the abrasive content is fine mesh silica and/or alumina powder in combination with a synthetic detergent and soap. The total solids-to-resin content of this product is of the order of about 4–5:1, the fine mesh abrasive constituting about 75% of the solids; and the synthetic detergent and the soap being present in approximately equal proportions.

Another industrial cleaner is one in which there are used in place of the oxide abrasives described in the foregoing, any one or a mixture of comminuted metals, such as metal filings of copper, aluminum, stainless steel, etc.

It will also be apparent that the skeletal structure of the products will provide for a variation in degrees of resiliency, depending upon the selection of the specific materials used to provide the resinous skeleton. Such selection is readily attainable in consequence of the known characteristics of foam or foam forming substances. Furthermore, these sponges can be provided with a variety of abrasives of various graded grit sizes and graded hardnesses. The selection of the abrasive components to provide desired abrading or polishing effect can readily be determined by preliminary testing based on the known qualities of the abrasives.

We have further found that when soap flakes and detergents (compatible with soaps) are both used as additives, it is advantageous to coat the granules of the synthetic detergents with soap, thus allowing for slower release of the detergent particles when the sponges are moistened.

Additives can be blended in a sponge according to this invention by making up a separate sponge each with one or more of the additives therein. Then the separate sponges are shredded and portions thereof are blended into a foam forming reaction mass prior to foam formation whereby a new sponge with desired proportions of additives is made.

Microencapsulation can be employed to introduce large amounts of oils or other additives into sponges. Microencapsulated oil ingredients are mixed into the foam forming reaction mass prior to foam formation. It is also feasible to introduce oils by means of an oil absorbing substance which substance can then be added to the foam forming reaction mass before foam formation.

It is clearly preferable to prepare preliminarily a carrier material containing the additive, which carrier material is then mixed into the reaction mass before foam formation begins, but it is possible also to proceed directly to manufacture of the sponges from a prepolymer and suitable additives, a so called "one shot" approach.

The following are examples in accordance with this invention.

EXAMPLE 1

Step I—Preparation of silicone-containing material

To a mass of 5 pounds of coco-tallow soap (low titer) in the form of large flakes, we add and gently incorporate 2 pounds of dimethyl silicone (viscosity 350 CPS) by letting the silicone flow onto the top of the mass of the soap flakes, and allow the mixture to stand for 5 minutes. We then mix the mass in such a way as to avoid substantial breaking of the flakes. To this mass we then add 12 additional pounds of the aforesaid soap flakes. The whole mass is handled to effectuate a thorough distribution of the silicone-coated soap flakes throughout the whole mass. To this we add 10 pounds of a linear alkylaryl sulfonate detergent in the form of strong beads. We then gently and thoroughly mix the entire mass to form a dry material containing the silicone.

Step II—Preparation of the foam former

A. 100 weight parts of polypropylene glycol (molecular weight 2,000, hydroxyl No. 56) are introduced in a reactor in an inert atmosphere. To the glycol are added 9.1 weight parts of tolylene diisocyanate. The mixture is rapidly agitated and the temperature raised to and maintained for 3 hours at 120° C. until the viscosity reaches 15,000 CPS (Brookfield method, 25° C.). There are then gradually added during 1 hour at 120° C., 24.5 weight parts of additional tolylene diisocyanate. This fluid is then brought to room temperature (about 20°–25° C.). This product is a prepolymer.

B. To 570 grams of the prepolymer produced in part A, there are added 35 grams of the following catalyst mixture:

| | |
|---|---|
| 1,4-bis-(2-hydroxypropyl)-2-methylpiperazine | 1.0 part |
| Triethanol amine | 0.5 part |
| Water | 1.9 parts |
| 50% aqueous emulsion of dimethyl silicone | 1.0 parts |

We mix the catalyst in the prepolymer and stir the mass until foam formation is initiated.

Step III—Incorporation of mixture produced in Step I with the foam former

When the mass produced in Step II begins to undergo foam formation, there are added 300 grams of the silicone-bearing material produced in Step I. The mass is thoroughly but gently mixed to avoid substantial fracturing and disintegration of the solid components of the mixture produced in Step I. The mixture is poured into an open mold. The mass is allowed to rise, gel and set. On cooling, the solid resilient mass is cut into blocks of convenient size to form the synthetic sponge product of this invention.

Part A of Step II, as mentioned, is directed to the formation of the prepolymer. Instead of preparing the prepolymer, commercially available prepolymers, such as for example, Resin F 202 (Nopco Chemical Co.), may be used for the manufacture of the foam former.

EXAMPLE 2

A synthetic sponge is manufactured in accordance with the general procedure described in Example 1, with the inclusion, however, of ethylene diamine tetraacetic acid, which functions as a rust inhibitor. In this procedure, the silicone is embodied with the soap flakes as described in Step I of Example 1. To the soap flakes containing the silicone (total mass of 17 pounds) there is added about ½ ounce of sodium salt of ethylene diamine tetraacetic acid (versene beads) which is thoroughly mixed into the material, care being taken to avoid breaking the soap flakes. The alkylaryl sulfonate is combined therewith as in Step I of Example 1.

EXAMPLE 3

A sponge is manufactured in accordance with the general method described in Example 1, which contains, in addition to the recited components, a small amount of a suitable ultraviolet light absorber, for example, 2,4-dihydroxy benzophenone. 15 grams of the ultraviolet light absorber are added at the stage in Step I just prior to the incorporation of the alkylaryl sulfonate beads. The compounded foam will then provide protection against degradation by sunlight, if used for example in automobile washing.

EXAMPLE 4

A sponge is made in accordance with the general procedure described in Example 1 with the inclusion, however, of both the aforesaid ultraviolet light absorber and the ethylene diamine tetraacetic acid.

The silicone sponge products made in accordance with this invention can have a silicone content as high as about 10 to 20% of the mass. Suitable results, especially in cleaning automobile bodies and the like, are attained when the silicone content of the sponge is about 4.5%.

EXAMPLE 5

To 1 pound of a 200 mesh cellulose flour are added 2 pounds of dimethyl silicone. After the silicone has been thoroughly absorbed, 27 pounds of a linear biodegradable alkylaryl sulfonate are added. This is thoroughly blended and mixed. The subsequent steps are the same as described in Example 1.

In the following examples, the general procedure of manufacture is that set forth in the foregoing examples. Accordingly, we will merely name the component materials and the amounts thereof in parts by weight.

EXAMPLE 6

| | |
|---|---|
| Prepolymer | 560 |
| Silicone-vehicle-silicone combination: | |
| Coco-tallow soap | 170 |
| Alkylaryl sulfonate | 100 |
| Dimethyl silicone | 27 |
| Catalyst system: | |
| Triethanolamine | 4 |
| 1,4-bis(2-hydroxypropyl)-2-methylpiperazine | 8 |
| 50% aqueous dimethyl silicone emulsion | 8 |
| Water | 8 |

EXAMPLE 7

| | |
|---|---|
| Propolymer | 560 |
| Silicone-vehicle-silicone combination: | |
| Coco-tallow soap | 150 |
| Alkylaryl sulfonate | 120 |
| Dimethyl silicone | 32.4 |
| Catalyst System: | |
| N-methyl-morpholine | 4 |
| Triethanolamine | 2 |
| 1,4-bis-(2-hydroxypropyl)-2-methylpiperazine | 4 |
| Diethanolamine | 2 |
| 50% aqueous dimethyl silicone emulsion | 8 |
| Water | 8 |

EXAMPLE 8

| | |
|---|---|
| Prepolymer | 560 |
| Silicone-vehicle-silicone combination: | |
| Coco-tallow soap | 160 |
| Alkylaryl sulfonate | 110 |
| Dimethyl silicone | 25 |
| Catalyst system: | |
| N-methyl-morpholine | 2 |
| Triethylamine | 1 |
| Triethanolamine | 3 |
| 1,4-bis-(2-hydroxypropyl)-2-methylpiperazine | 6 |
| 50% aqueous dimethyl silicone emulsion | 8 |
| Water | 8 |
| Rust preventive: | |
| Sodium salt of ethylenediamine tetraacetic acid | 4 |
| Ultraviolet light absorber: | |
| 2-hydroxy-4-methoxy-benzophenone | 1 |

EXAMPLE 9

| | |
|---|---|
| Prepolymer | 560 |
| Silicone-vehicle-silicone combination: | |
| Coco-tallow soap | 140 |
| Alkylaryl sulfonate | 130 |
| Dimethyl silicone | 25 |
| Catalyst system: | |
| Triethanolamine | 4 |
| 1,4-bis-(2-hydroxypropyl)-2-methylpiperazine | 5 |
| N,N,N',N'-tetramethyl-1,3-butanediamine | 3 |
| 50% aqueous dimethyl silicone emulsion | 9 |
| Water | 7 |
| Rust preventive: | |
| Sodium salt of ethylenediamine tetraacetic acid | 3 |
| Ultraviolet light absorber: | |
| Benzotriazone compound (as for example, Tinuvin P) | 1 |

EXAMPLE 10

| | |
|---|---|
| Prepolymer | 560 |
| Silicone-vehicle-silicone combination: | |
| Coco-tallow soap | 120 |
| Alkylaryl sulfonate | 150 |
| Dimethyl silicone | 25 |

-continued

| Catalyst System: | |
|---|---|
| Triethanolamine | 4 |
| 1,4-bis-(2-hydroxypropyl)-2-methylpiperazine | 5 |
| Octadecyl dimethylamine | 3 |
| 50% aqueous dimethyl silicone emulsion | 8 |
| Water | 8 |

EXAMPLE 11

Substitute in Example 1, etc., 3 parts per 100 parts of resin mix, the following as the catalyst:

| | | |
|---|---|---|
| Triethanolamine | 80 | parts |
| Water | 160 | |
| Triethylenediamine | 12 | |
| Silicone Surfactant (L 530 of Union Carbide or Dow Corning 100, etc.) | 40 | |
| Dibutyl Tin Laurate | 0.2 | |
| Quadrol (Wyandotte Chemical Co.) n,n,n$^1$,n$^1$,-Tetrakis (2 hydroxypropyl) ethanolaminidiamini | 15 | |

A marked advantage of the synthetic sponge made in accordance with the foregoing examples is that during cleaning of an automobile body or the like, it does not remove the wax coatings desposited thereon, as by Simonizing or porcelainizing. A further advantage of the sponge is that when the sponge is immersed in water, the aqueous solution thus produced is at a pH which is substantially neutral.

The selection of the component materials constituting the novel products of the foregoing examples and the proportioning thereof may be varied. The choice of the component materials to be used and suitable proportioning thereof are determined easily by laboratory tests. The materials and the amounts thereof set forth in the various examples are those which we have found to be readily available and which give very suitable results. For instance, the alkylaryl sulfonate mentioned in the examples is the sodium salt of dodecyl benzene sulfonate. It is among the most widely used of the syndets. It is marketed by many of the largest manufacturers under well known trademarks, and is also available as an amine salt. However, other surfactants, particularly those which are biodegradable are also useful, including linear alcohol sulfates, sulfated fatty acids, amides, and esters, glycol esters, fatty alkanalamides, ethoxylated alcohols and phenols.

The sponges made in accordance with the foregoing examples are useful in consequence of their high silicone content, for cleaning of automobile bodies and for many other cleaning purposes. When used in cleaning panes of glass, the effect thereof is to prevent misting or steaming thereof. When applied, for example, to windshields the effect is very substantially to reduce fogging, or accumulation of water while driving through rain. A similar effect is observed in ski goggles and bathroom mirrors.

Another advantage of the sponges in accordance with the foregoing examples is that when washing an automobile, it is possible to clean the same without scratching, removing the paint, or removing the finishes thereon imparted by previous waxings or similar treatments, and at the same time effectively to polish the body.

Another advantage is carrying out cleaning operations with sponges made in accordance with the foregoing examples is that after rinsing with clear water, it is unnecessary to follow up with a drying or wiping cloth.

It will be apparent, therefore, that we have provided the art with a resilient synthetic sponge containing a large amount of silicone "built into" the sponge structure. As has been stated, the achievement of such a sponge has resulted from our discovery that we could introduce a large amount of silicone into the mass undergoing foaming in such fashion that the reactive mass is insulated or isolated from the large amount of silicone.

EXAMPLE 12

A Resilient Abrasive Sponge Product

Preparation of the abrasive content.

A mass of abrasive particles, as for example, silica (mesh size 40–60), is heated until the temperature thereof is about 65°–75° C.

Preparation of the foam former.

100 weight parts of polypropylene glycol (molecular weight about 2,000, hydroxyl No. 56) are introduced into a reactor in an inert atmosphere, as for example, nitrogen. To the glycol there are added 9.1 weight parts of tolylene diisocyanate. The mixture is rapidly agitated and the temperature raised to and maintained for 3 hours at 120° C. until the viscosity reaches 15,000 CPS (Brookfield method 25° C.). There is then gradually added during 1 hour at 120° C., 24.5 weight parts of additional tolylene diisocyanate. This fluid is brought to room temperature (about 20°–25° C.).

To 100 weight parts of this fluid is added a mixture of 2.3 weight parts of water and 2.0 weight parts of N-methyl morpholine; and the mass is stirred for 5 seconds.

Mixing of the abrasive with the foam former.

500 parts by weight of the hot abrasive particles (having a temperature as above) are mixed with 100 weight parts of the foam former (prepared as above), and the whole mass is vigorously stirred for about 50–60 seconds to assure uniformity of distribution of the resin in the viscous mass. The viscous mass is poured into a suitable mold (open cavity). The mass rises, gels and cures in about 3 to 8 minutes. In general, the abrasive particles should be at a temperature of 65 to 125° C.

On cooling, the solid resilient mass is cut into pads or blocks of convenient size to form scouring pads or blocks.

For the continuous manufacturing of the product, a stream of the hot abrasive particles, a stream of the foam former, and a stream of the catalyst are proportioned to feed simultaneously into a high speed mixing head provided with a continuous discharge. The discharged mixture thus is fed continuously into suitable molds.

The products can be suitably colored or tinted by including a suitable pigment or tinctorial agent in any of the ingredients.

EXAMPLE 13

In accordance with the general procedure described in Example 12, a scouring and cleaning product is manufactured wherein the solids content includes a suitable soap, as for example, a coconut oil soap. The abrasive grits-to-soap ratio is (by weight) 350:70.

EXAMPLE 14

In accordance with the general procedure described in Example 13, a product is prepared in which in lieu of soap alone as the cleaning agent, there is employed a synthetic detergent with soap. The detergent and the soap are mixed preliminarily, as by tumbling, to effectuate a coating of synthetic detergent particles. The detergent particles employed can be the sodium alkyl sulfates, e.g., sodium cetyl sulfate, or sodium alkylaryl sulfonates, or the sodium salts of sulfonic acid derivatives of dialkyl dicarboxylates in the following approximate proportions: sodium alkyl sulfate, 40 parts; soap, 180 parts.

There may also be included therewith about 10 parts of carboxymethyl cellulose.

EXAMPLE 15

A product as prepared in accordance with the general procedure described in Example 12, except that in place of the mixture of the water and the N-methyl morpholine, there is used as the catalyst at 3% solution of sodium alginate in water.

EXAMPLE 16

Products akin to those described in Examples 13 and 14 are likewise prepared in which the catalyst is the 3% aqueous solution of sodium alginate just mentioned.

EXAMPLE 17

A product as made in accordance with the general procedures described in Examples 12 and 13, that is, using either of the catalysts mentioned, in which in lieu of the oxide abrasive particles there is employed a mass of comminuted metals, such as iron, stainless steel, aluminum, copper, brass, etc.

Although the skeleton-former described in the foregoing Examples 12-17 is currently preferred, other foam or sponge-forming resinous materials well known in the art can be used. The important feature is the high temperature of the abrasive particles when mixed with the foam former. The heat of those particles makes it possible to achieve and maintain uniform distribution of the large mass of the abrasive particles throughout the mixture thereof with the comparatively small amount of the foam former; and to accomplish the rapid rise, gelation and cure of the mixture.

It will also be understood that the cellular structure of the final abrasive product can be varied from sponge to foam character, including intermediate combinations thereof, depending upon the use of an open mold or a closed mold, with, in the case of the latter, control of the pressure.

EXAMPLE 18

Microencapsulation

Step I—Microcapsules of oils or silicone components are prepared as follows: 1100 grams of gelatin are dissolved in 1.8 liters of water bring the water temperature to not more than 54° to 55° C. 1000 grams of gum arabic are dissolved in 1.8 liters of water under the same condition.

Step II—The warm solution from Step I are mixed in a suitable container and heated to exactly 55° C. The solution is stirred and the pH value adjusted to 4.65 by addition of either 0.1 N NaOH or 0.1 N HCl.

Step III—Oil fractions are added as follows: 9 kilos of isopropyl palmitate are added to the mixture with vigorous stirring, the mixture is cooled slowly with stirring and the mixing is continued until the temperature reaches 10° C.

Step IV—The microcapsules are separated from the aqueous solution and dried. The microcapsules are dried by treatment with suitable solvents. The size distribution of the microcapsules are determined by speed of stirring, by the amount of oil and by microcapsules wall components.

In the following examples, the general procedure of foam manufacture is according to the so called "one shot" system.

EXAMPLE 19

| | | |
|---|---|---|
| Pluracol Polyol G P 3030 | 100 | gms. |
| Hydroyl number 56 (Wyanodotte Chemical Co.) | | |
| Catalyst system per Example 11 | 2.6 | gms. |
| Tolylene diisocyanate (TDI) | | |
| 80/20 mixture of 2, 4/ 2, 6 isomers | 37.8 | gms. |

The catalyst is added to the polyol and blended. The TDI is then added. The mixture is stirred rapidly until it begins to cream. At this stage 30 gms. of a mixture consisting of 60% coco tallow soap and 40% of biodegradable linear alkyl aryl sulfonate (such as Sulframin 85 at Witco Chemical Co.) is added. The stirring is continued until the soap mix is uniformly dispersed. The mix is then poured into a suitable mold and left to foam.

EXAMPLE 20

| | | |
|---|---|---|
| Pluracol TP 4040 Polyol (Wyandotte Chemical Co.) | 70 | gms. |
| Pluracol TPE Polyol (Wyandotte Chemical Co.) | 30 | gms. |
| Catalyst (same as in Example 19) | 2.6 | gms. |
| Tolylene diisocyanate | 35.6 | gms. |

The procedure is the same as for Example 18.

EXAMPLE 21

Foaming bath sponge

| | |
|---|---|
| Olefin Sulfate (Sulframin of Witco Chemical Co.) | 250 gms. |
| Coco Tallow Soap | 50 gms. |
| Hypoallergenic Lanolin Derivative (Solulan 95 of Amerchol Chemical Co.) | 10 gms. |

The Solulan 95 is added to the soap flakes and mixed with the Olefin Sulfate.

| | |
|---|---|
| Prepolymer | 100 gms. |
| Catalyst | 3 gms. |

EXAMPLE 22

Soap-Detergent Mix

| | |
|---|---|
| As in Example 21 | 40 gms. |

Mix the prepolymer and catalyst blend until creaming is uniform. Add the soap mix, stirring until dispersed uniformly. Pour into suitable molds.

This example can also be a sponge for a pet (dog or cat or the like) by addition of a suitable pesticide.

EXAMPLE 23

Bath Oil Mix

| | |
|---|---|
| 1. Modulan acetylated lanolin (Amerchol Chemical Co.) | 5.0% |
| 2. Acedulan acetylated lanolin alcohols (Amerchol Chemical Co.) | 5.0 |
| 3. Isopropyl Myristate | 25.0 |
| 4. Mineral Oil, 70 Vis. | 60.0 |
| 5. Polyethylene 400 Dilaurate | 5.0 |
| 6. Perfume | q.s. |

This is absorbed on 12–15 gms. of Strickite oil collector per U.S. Pat. No. 3,657,125 until it is practically a solid gel.

This is used as follows:

| | |
|---|---|
| Prepolymer | 100 gms. |
| Catalyst | 3 gms. |

Mix until uniform creaming begins. Add the bath oil mix. Stir rapidly until dispersed. Pour into suitable molds to complete foaming.

EXAMPLE 24

Detergent sponge with scrubber top

To a sponge sheet prepared in accordance with Example 19, the following is knife coated or roller coated on teflon rolls.

| | |
|---|---|
| Prepolymer | 100 gms. |
| Catalyst | 2.5 gms. |
| Dow Corning 100 Silicone | 2.0 gms. |

Thoroughly mix until uniform creaming is observed. The following formulaes added and then stirred until foaming begins. After foam rises it collapses and bubbles. At this stage a very thin layer is coated on the sponge sheet. This can be done on a batch or a continuous basis. A hard flexible scrubbing surface is formed on the sponge sheet.

| | |
|---|---|
| *Lipo Foam (Lipo Chemical Corp.) | 24 gms. |
| Emcco L CDA | 2.5 gms. |
| Water | 25 gms. |

*Use 5 gms. per 100 gms. of prepolymer.

EXAMPLE 25

Detergent abrasive sponge (iron rust)

| | |
|---|---|
| Prepolymer | 100 gms. |
| Catalyst | 3 gms. |

Mix until mixture begins to cream. Add rapidly the following:

30 gms. of Soap Mix
150 gms. of Abrasive or Aluminum Oxide

Mix at high speed until mix is uniform and pour into suitable molds.

| Soap Mix: | 60% Coco Tallow Soap in flakes or granules |
|---|---|
| | 40% Linear Alkyl Aryl sulfonate (Biodegradable) |
| Abrasive Mix: | Stainless Steel 60–80 Mesh 80% |
| | Stainless Steel 240 Mesh 20% |
| Aluminum Oxide: | 60–80 Mesh 100% |

EXAMPLE 26

Detergent abrasive sponge

Soap Mix:

| | |
|---|---|
| Coco tallow soap | 60% |
| Linear alkyl aryl sulfonate | 40% |

30–40 gms. per 100 gms. of prepolymer
40–60 gms. to 100 gms. of polyol

Abrasive:

| | | |
|---|---|---|
| Stainless Steel | 80 mesh | 80 gms. |
| Stainless Steel | 240 mesh | 20 gms. |

EXAMPLE 27

Detergent abrasive sponge

| | |
|---|---|
| Coco tallow soap | 60% |
| Linear alkyl aryl sulfonate | 40% |
| Abrasive Mix: 80–100 mesh $AL_2$ $AL_2$ $O_3$ | |

EXAMPLE 28

Bubble shower bath sponge

| | |
|---|---|
| Solulan C-24 | 5% |
| Ethoxylated lanolin derivative (Amerchol Chemical Co.) | |
| Hexylene Glycol | 10% |
| Alkyloamide of coconut fatty acid and diethanolamine | |
| Monamide 150 AD (Mona Industries, Inc.) | |
| Triethanolamine lauryl sulfate | 65% |

Warm to melt solution C24. Mix thoroughly. Absorb on about 15 gms. of Strickite oil collector per U.S. Pat. 3,657,125 until appearance is that of a solid gel.

| | |
|---|---|
| Prepolymer | 100 |
| Catalyst | 3 |

Mix until uniformly creamed. Add the above mix, stirring rapidly. Pour into suitable molds.

It will be understood that the foregoing description of the invention and the examples set forth are merely illustrative of the principles thereof. Accordingly, the appended claims are to be construed as defining the invention within the full spirit and scope thereof.

We claim:

1. A method for manufacturing a resilient scouring product characterized by the feature that a hot mass of abrasive particles is thoroughly mixed with a mixture of an aryl diisocyanate and a polyether, including as a catalyst an alkali metal or ammonium salt of alginic acid, and the mass is allowed freely to expand and cure thereby to form a synthetic sponge structure.

* * * * *